United States Patent
Uda et al.

(10) Patent No.: US 7,440,118 B2
(45) Date of Patent: Oct. 21, 2008

(54) APPARATUS AND METHOD FOR COLOR FILTER INSPECTION

(75) Inventors: Mitsuru Uda, Shiga (JP); Atsushi Kohayase, Kanagawa-Ken (JP); Hiroshi Yamashita, Kanagawa (JP)

(73) Assignee: International Business Machines Corporation, Armonk, NY (US)

( * ) Notice: Subject to any disclaimer, the term of this patent is extended or adjusted under 35 U.S.C. 154(b) by 334 days.

(21) Appl. No.: 11/419,030

(22) Filed: May 18, 2006

(65) Prior Publication Data

US 2006/0290922 A1    Dec. 28, 2006

(30) Foreign Application Priority Data

Jun. 24, 2005    (JP)    ............... 2005-184323

(51) Int. Cl.
*G01B 11/30*    (2006.01)
(52) U.S. Cl. .................................. 356/600; 356/239.2
(58) Field of Classification Search ................. 356/600, 356/237.1–237.5, 239.1–239.8; 430/7, 30
See application file for complete search history.

(56) References Cited

U.S. PATENT DOCUMENTS

| | | | | |
|---|---|---|---|---|
| 5,400,135 A | * | 3/1995 | Maeda | ..................... 356/239.1 |
| 5,773,173 A | * | 6/1998 | Nakano et al. | ................. 430/30 |
| 6,221,544 B1 | * | 4/2001 | Hayashi et al. | ................. 430/7 |
| 6,842,240 B2 | * | 1/2005 | Ueta | ..................... 356/239.2 |

FOREIGN PATENT DOCUMENTS

| | | | |
|---|---|---|---|
| JP | 3057945 A | | 3/1991 |
| JP | 3189545 A | | 8/1991 |
| JP | 8122271 A | | 5/1996 |
| JP | 09-126948 | | 5/1997 |
| JP | 2003149163 | | 5/2003 |
| JP | 2003344299 | * | 12/2003 |
| JP | 2005121500 | | 5/2005 |
| JP | 2006125936 | * | 5/2006 |
| JP | 2006284217 | * | 10/2006 |
| JP | 2007327761 | * | 12/2007 |

* cited by examiner

*Primary Examiner*—Hoa Q Pham
(74) *Attorney, Agent, or Firm*—Yuanmin Cai

(57) ABSTRACT

The present invention provides an apparatus and method for detecting flatness and/or unevenness of a surface of an overcoat layer on a colored pixel layer of a color filter with a high degree of accuracy. The apparatus includes: a light source 34, placed almost directly above the surface of a plate 30, for emitting an emission-line spectrum corresponding to at least one color of coloring particles in a color filter 32; a photo-receiver 36, placed obliquely upward with respect to the surface of the plate 30 and having a spectral sensitivity corresponding to the emission-line spectrum of the light source, for receiving reflected light from the color filter 32 on the plate 30 during inspection; and a detection means 42 for creating a brightness distribution for a color using a color signal output from the photo-receiver 36 as corresponding to its spectral sensitivity to detect the flatness (unevenness) of the surface of an overcoat layer 16.

18 Claims, 5 Drawing Sheets

APPARATUS AND METHOD FOR COLOR FILTER INSPECTION

CROSS-REFERENCE TO RELATED APPLICATIONS

The present application claims the benefit of priority of a Japanese Patent Application No. 2005-184323, filed Jun. 24, 2005 with the Japan Patent Office, the content of which is incorporated herein by reference in its entirety.

FIELD OF THE INVENTION

The present invention relates generally to an apparatus and method for color filter inspection, and more particularly, to an apparatus and method for detecting flatness and/or unevenness of a surface of an overcoat layer forming an uppermost layer of a color filter.

BACKGROUND OF THE INVENTION

A color filter used in a liquid crystal color display or the like generally has a colored pixel part (array), formed on a transparent substrate such as glass and corresponding to three primary colors, namely, red (R), green (G), and blue (B). The methods of manufacturing the colored pixel array may include the following four types: dyeing, pigment dispersion, printing, and electro-deposition. Among these four methods, the pigment dispersion method is excellent in terms of performance and production costs. Therefore, the pigment dispersion method is widely used today, and is expected to remain dominant in the future.

In the pigment dispersion method, a color resist is applied to the surface of a substrate using a spin coater or dye coater, and the color resist layer is patterned using, for example, a photolithography technique. This process is repeated for each color in due order (e.g., for R, G, and B in this order) to form a three-color (RGB) pixel array. In this case, the second-applied color resist (e.g., G) is affected by the first-applied color resist pattern (e.g., R) to make the thickness of the second color resist uneven (that is, to cause uneven application). Similarly, the third color resist (e.g., B) is affected by the underlying two-color resist patterns to make the thickness of the third color resist uneven. Since the thickness of each color resist layer may affect the spectral characteristics of light, it is desirable that the thickness of each color resist layer be made as uniform as possible.

An overcoat layer is applied to, or coated over, the surface of the colored pixel array as a protective layer using the coater in the same manner as those of the color resist layers. The surface of the overcoat layer needs to be as flat as possible. This is because, if the surface of the overcoat layer is not flat (that is, if it is uneven), liquid crystal cannot be filled in every corner uniformly and accurately in the following process. However, since the application of the overcoat layer is also affected by the underlying colored pixel array, the application of the overcoat layer is likely to be uneven. This can make the surface of the overcoat layer uneven.

Despite the importance given to the management of the surface flatness (unevenness) of color resist layers and an overcoat layer constituting a color filter, there is yet no apparatus capable of inspecting the flatness (uneven application) of these layers accurately. Under present circumstances, the reliability of inspection depends on visual inspection by skilled inspectors.

As a related art document, for example, Japanese Patent Laid-Open No. 09-126948 discloses a method of inspecting scratches on, or unevenness of, the surface of a color filter. In this method, reflected light from the color filter is measured while rotating a substrate at constant or uniform speed in order to prevent a pixel edge part of the color filter from being detected as a pseudo defect. However, this publication does not disclose ways of detecting the flatness (unevenness) of the surfaces of color resist layers and an overcoat layer inherent in the pigment dispersion method.

SUMMARY OF THE INVENTION

It is an object of the present invention to provide an apparatus and method to detect, with a high degree of accuracy, the flatness (unevenness) of the surface of an overcoat layer formed over a colored pixel layer of a color filter.

It is another object of the present invention to detect variations in the thickness (surface unevenness) of the colored pixel layer underneath the overcoat layer of the color filter.

According to one embodiment of the present invention, a color filter inspection apparatus is particularly characterized by comprising:

a light source, placed almost directly above the surface of a plate, for emitting an emission-line spectrum corresponding to at least one color of coloring particles in a color filter;

a photo-receiver, placed obliquely upward with respect to the surface of the plate and having a spectral sensitivity corresponding to the emission-line spectrum of the light source, for receiving reflected light from the color filter on the plate during inspection; and detection means for creating a brightness distribution for the color using a color signal output from the photo-receiver as corresponding to its spectral sensitivity to detect the flatness (unevenness) of the surface of an overcoat layer.

According to one embodiment of the color filter inspection apparatus (method) of the present invention, the light source emits the emission-line spectrum corresponding to at least one color of the coloring particles in the color filter, and the photo-receiver has a spectral sensitivity corresponding to the emission-line spectrum of the light source. This structure makes it possible to detect the amount of reflected light corresponding to the color accurately (at high resolution). Therefore, the thickness of a pixel layer corresponding to the color and the unevenness (non-uniformity) in the thickness of a transparent overcoat layer formed over the pixel layer may be detected with high sensitivity as a distribution of the reflected light amount (brightness) from a macroscopic viewpoint.

DETAILED DESCRIPTION OF THE INVENTION

Figure 1:
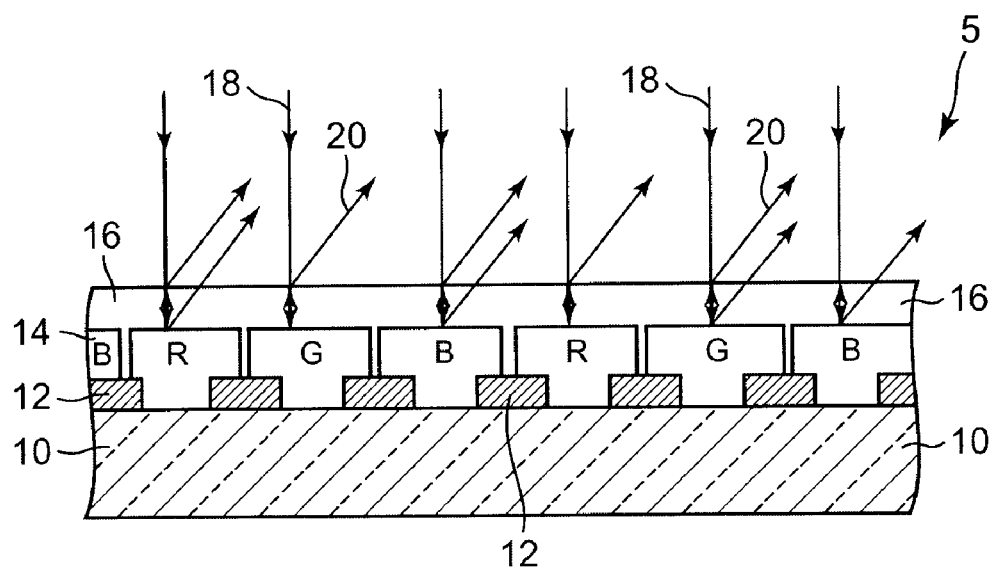
FIG. 1 is a schematic illustration of a color filter and the detection principle according to one embodiment of the present invention.

An inspection apparatus of the present invention will now be described with reference to the accompanying drawings. First, the detection principle of the present invention will be described. FIG. 1 is a schematic illustration of a color filter and the detection principle according to one embodiment of the present invention. As shown, a black matrix layer pattern 12 is formed on a transparent substrate 10, and a three-colored (RGB) pixel layer pattern 14 is formed over the black matrix layer pattern 12 on the transparent substrate 10. The colored pixel layer 14 is formed by a pigment dispersion method. The pigment dispersion method uses color resists, each formed by dispersing a pigment as a coloring agent uniformly into a transparent resin (PVA or acrylic resin). Each color resist is applied to, or coated over the substrate 10 using a spin coater or dye coater. Then, after the color resist is semi-cured (pre-baked), the color resist layer is patterned using a photolithography technique (exposure and development). This process is repeated for each color in due order (e.g., for R, G, and B in this order) to form the three-colored (RGB) pixel layer (array) 14. After that, an overcoat layer 16 made of a transparent resin is formed on the pixel array layer 14.

Upon inspection, the substrate 10 is irradiated from above with light having an emission line or narrow spectral band, which appears in an emission line spectrum as corresponding to one color of the coloring particles in the color resist layer. In FIG. 1, light having an emission line, e.g., green (G), is irradiated. The irradiated light 18 interferes between the color resist layer 14 and the overcoat layer 16, and comes out from the surface of the overcoat layer 16 as reflected light. According to one embodiment of the present invention, light 20 reflected obliquely upward from the overcoat layer 16 may be used.

The particle diameter, or size, of pigment particles in each color resist may be about 0.07-0.3 μm. The particle size ranges from that equivalent to the range of visible light wavelengths (0.4-0.6 μm) to one-tenth of the visible light band. Therefore, the reflected light 20 from the pigment particles may become Mie scattered light. The term "Mie scattering" means a phenomenon that only the light traveling direction is changed (scattered) without any change in wavelength and energy of light (elastic scattering). The reflected light 20 as Mie scattered light has directivity. Focusing attention on the relationship between the particle size of the pigment particles and the wavelengths of irradiated light, the present invention uses the directional reflected light (Mie scattered light) 20. In other words, according to one embodiment of the present invention, the directional reflected light (Mie scattered light) 20 may be received by a photo-receiver.

Since the irradiated light 18 contains the emission line or spectral band of green (G), the amount (intensity) of reflected light from the green color resist becomes larger than those from the other red and blue color resists. This green reflected light is received by a photo-receiver (not shown). The photo-receiver is sensitive to green light. Therefore, the photo-receiver detects more reflected light from the green color resist at higher resolution than those from the other color resists. In other words, since green light is irradiated on green colored pixels, and reflected light from the green colored pixels is received by the photo-receiver sensitive to green light, noise components containing light components of the other colors may be eliminated, achieving a high S/N ratio. The same holds true with regard to the use of other colors such as red and blue.

The amount of green light detected through the photo-receiver may vary depending on the unevenness (variations) in the thickness of the green color resist 14 and the unevenness (variations) in the thickness of the overcoat layer 16. The amount of green reflected light may be measured across the entire substrate and displayed as its brightness distribution. Thus, a distribution (map) representing the unevenness (variations) in the thickness of the green color resist 14 and the unevenness (variations) in the thickness of the overcoat layer 16 across the entire substrate may be obtained. In other words, the variations in the thickness of the color resists and the overcoat layer in the color filter substrate may be observed.

Here, if the green color resist is first formed, the unevenness in the thickness of the green color resist is smaller than those of the second- and third-formed red and blue color resists. This is because the first-formed color resist pattern has no underlying color resist pattern, and hence there is no influence of the underlying color resist pattern. Therefore, in this case, the reflected light 20 reflects more unevenness in the thickness (or flatness of the surface) of the overcoat layer 16. In other words, the unevenness in the thickness of the overcoat layer 16 may be detected accurately. On the other hand, if light containing a spectral band of red or blue light corresponding to the second or third color resist, the photo-receiver may obtain not only the unevenness in the thickness of the overcoat layer 16, but also unevenness information containing the influence of the unevenness in the thickness of the red or blue resist.

The above gives the outline of the detection principle according to one embodiment of the present invention. Note that the above description takes as an example the use of a green emission line, but the same holds true with regard to the use of a red or blue emission line. Furthermore, the irradiated light 18 may contain either a single-color emission line or two- or more-color emission lines.

Figure 2:
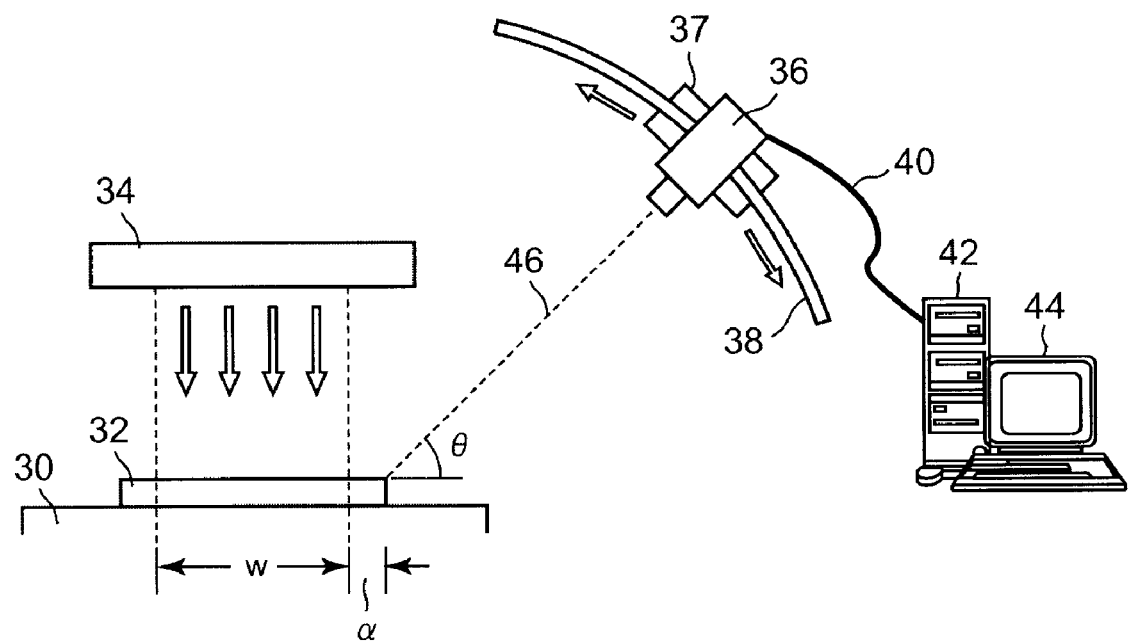
FIG. 2 is a sectional view showing the structure of a detector according to one embodiment of the present invention.

FIG. 2 is a sectional view showing a detector according to one embodiment of the present invention. Upon inspection, an inspected color filter 32 may be placed on a plate 30. The color filter 32 may have the same or similar structure as that indicated by reference numeral 5 in FIG. 1. A light source 34 is located almost directly above the surface of the plate 30. The plate 30 is movable in the horizontal (X-axis) direction by means of a plate moving mechanism (not shown). The plate 30 may be moved to change the irradiation range of the light source 34 over the color filter 32. A photo-receiver 36 is located obliquely upward with respect to the surface of the plate 30. The photo-receiver 36 may be moved along a rail 38 by a moving mechanism 37. The output of the photo-receiver 36 may be sent to detection means 42 through a cable 40.

The light source 34 irradiates light onto an area (W) of the surface of the color filter 32. The light source 34 has an emission-line spectrum containing at least one emission line corresponding to one of the colors of coloring particles. The light source 34 may be a fluorescent lamp or an electric discharge tube.

Figure 3:
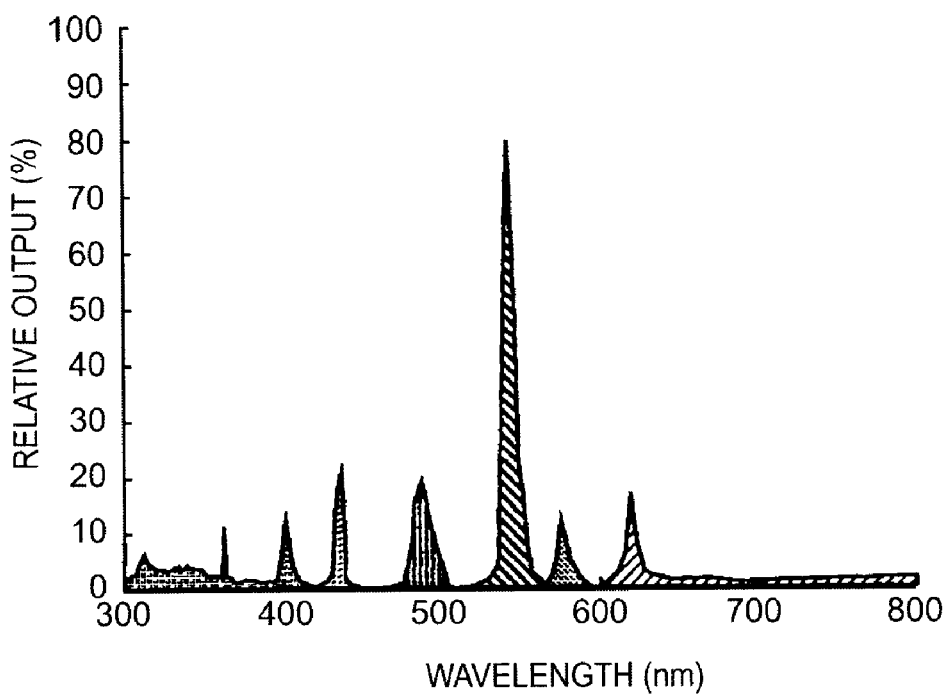
FIG. 3 is a line chart showing an example of the spectrum of a fluorescent lamp.
Figure 4:
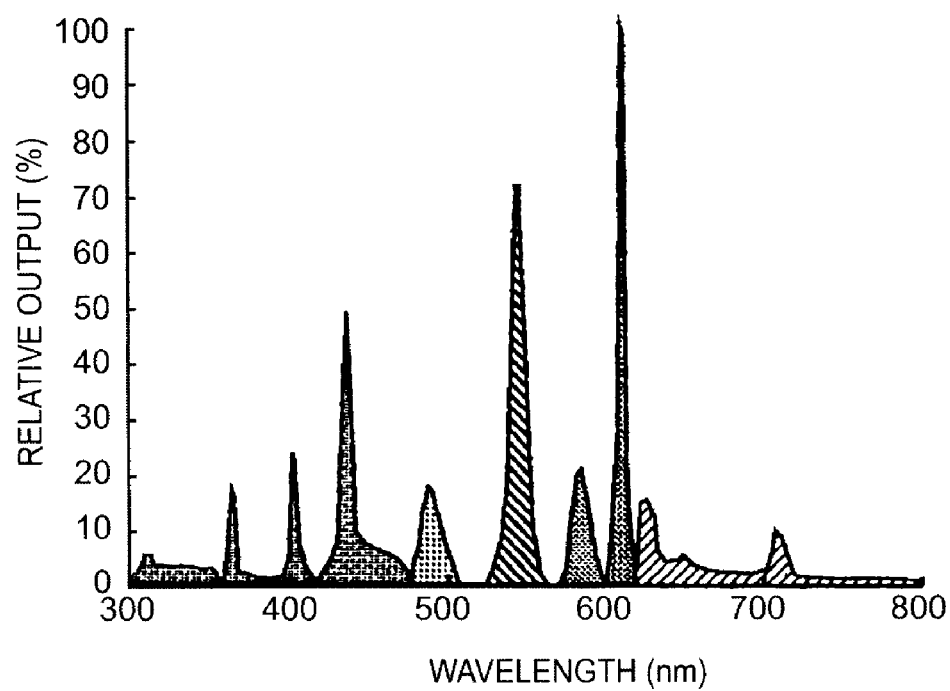
FIG. 4 is a line chart showing an example of the spectrum of another fluorescent lamp.

FIG. 3 is a line chart showing an example of the spectrum of a fluorescent lamp. The fluorescent lamp of FIG. 3 has a single emission line, for example, of green color. The peak of the emission-line spectrum may be around 540 nm but the invention is not limited in this respect. FIG. 4 is a line chart showing an example of a fluorescent lamp emitting an emission-line spectrum having, for example, three spectral lines, namely blue, green, and red emission lines. The peaks of the emission-line spectrum may be around 430, 540, and 620 nm, respectively. However, the invention is not limited in this respect either and other numbers of spectral lines at other peak wavelengths may be used.

Figure 5:
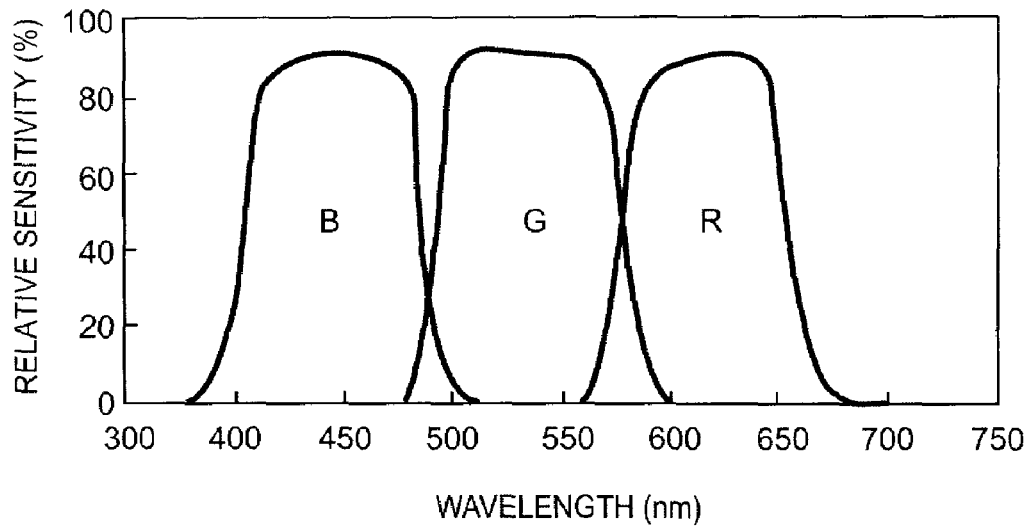
FIG. 5 is a curve chart showing an example of spectral sensitivities of a 3-CCD color line-scanning camera.

It is preferable that the half-bandwidth of the emission spectrum be in a range of 15-30 nm. This is because, if the half-bandwidth is too narrow, interference light increases more than enough, resulting in a reduction in detection sensitivity. On the other hand, if the half-bandwidth is too wide, scattered light increases more than enough, also resulting in a reduction in detection sensitivity. For a similar reason, it is preferable that the wavelength sensitivities of the photo-receiver 36 (FIG. 2) to those other than the emission-line spectrum of the light source should be as low as possible. The photo-receiver 36 may have a spectral sensitivity corresponding to the emission-line spectrum of the light source. For example, when the fluorescent lamp in FIG. 3 is used as the light source, the photo-receiver 36 is required to be highly sensitive to the emission line of the fluorescent lamp. On the other hand, in case of FIG. 4, the photo-receiver 36 needs to be highly sensitive to one or more of the three emission lines. It is desirable that the photo-receiver be a line sensor camera, for example, a CCD color line-scanning camera. This camera may be either a single-CCD camera or a three-CCD camera. In the case of the fluorescent lamp in FIG. 3, a camera using a single-CCD for green may be sufficient. In the case of the fluorescent lamp in FIG. 4, the camera may be either of a single-CCD type or a three-CCD type. FIG. 5 is a curve chart showing an example of spectral sensitivities of a three-CCD color line-scanning camera. In this case, each CCD corresponds to each color, R, G, or B, that is, each CCD has a spectral sensitivity to R, G, or B, respectively.

The moving mechanism 37 for moving the photo-receiver 36 may be either manually or automatically operated as long as it may move the photo-receiver 36 along the rail 38. The moving mechanism 37 shown in FIG. 2 is installed integrally with the photo-receiver 36, and controlled by the detection means 42. The photo-receiver 36 is moved along the rail 38 to change the angle θ with respect to the surface of the color filter. The photo-receiver 36 is positioned at a location where it does not receive specular reflection of light from the color filter 32. In other words, the photo-receiver 36 is so positioned that the center line 46 of the photo-receiver 36 comes to a position distance α away from the irradiation range W of the light source. The angle θ is so determined that the sensitivity of the photo-receiver 36 becomes high.

The detection means 42 receives output signals from the photo-receiver 36 through the cable the 40. Then, among the output signals from the photo-receiver 36, the detection means 42 uses one color signal corresponding to one of spectral sensitivities of the photo-receiver 36 to create an image map of the color filter (pixel array) according to the brightness (shades of gray, or light-and-dark pattern) of the color. The image map may also be in the form of a graph representing a brightness distribution on the substrate. If information on the entire substrate cannot be acquired at a time, then brightness information is accumulated sequentially in an internal memory of the detection means. Then, upon completion of acquiring all measures across the entire substrate, the brightness information is processed to display the information processing results on a display monitor 44 as an image map or brightness distribution graph. The flatness (unevenness) of the surface of the overcoat layer of the color filter may be detected as a variation in the shades of gray (or the light-and-dark pattern) of the image map, or a change in the brightness distribution graph. In other words, a place where brightness of the image changes may correspond to an uneven area of the overcoat layer. The detection means 42 also serves to control the moving mechanism 37. The detection means 42 controls the moving mechanism 37 to optimize the position of the photo-receiver 36 in order to improve the detection sensitivity.

As shown in FIG. 3, when the single-color light source and the camera having a single CCD corresponding to the color are used, a luminance signal from the color component is output as the output signal of the camera. Therefore, the output signal is processed to create the image map (brightness distribution). On the other hand, as shown in FIG. 4, when the light source having multiple emission lines and the camera having multiple CCDs are used, the output signal of the camera may not be used intact. This is because the output signal of such a camera is generally a composite signal in which multiple color components are combined. Since the signal required in the present invention is just one color signal corresponding to a specific color of pixels, only information on the corresponding color signal needs to be acquired separately from the other color signals. In this case, if the three-CCD camera is of the type that combines the outputs of the three CCDs through an image processing circuit, the output of a CCD corresponding to the specific color may be extracted before combined.

Figure 6:
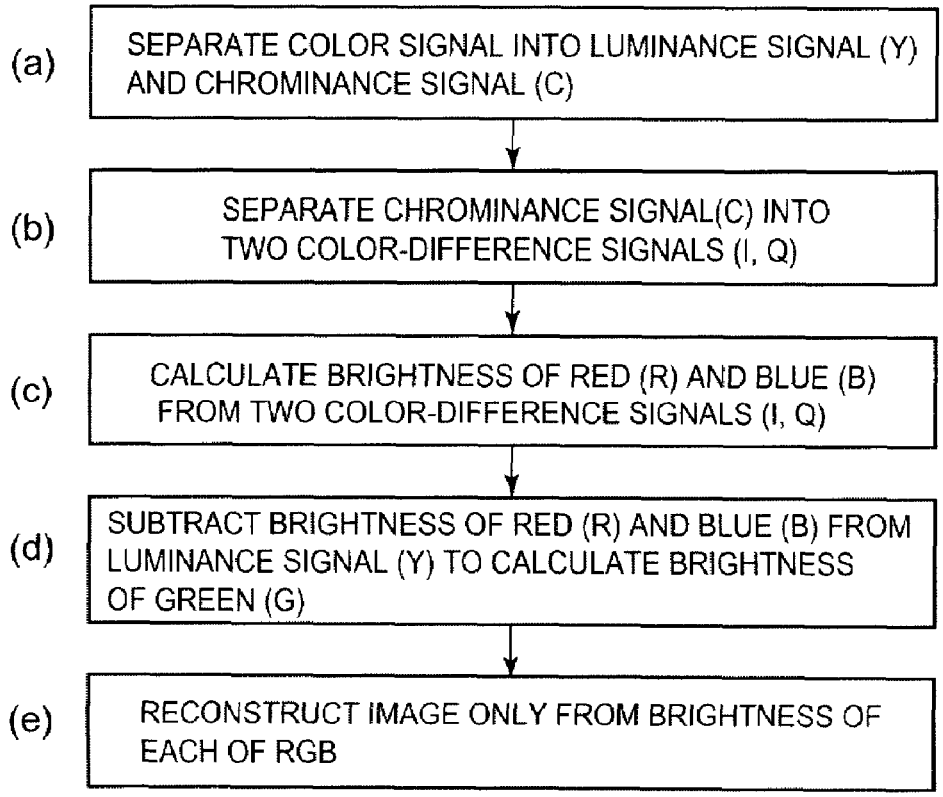
FIG. 6 is a flowchart showing a flow of separating a luminance signal for each color of R, G, B from a color signal.

On the other hand, if the output of one CCD cannot be acquired separately from the other outputs before combined, only the information (brightness information) on the specific color may be acquired according to a separation flow as shown in FIG. 6 to create the image map (brightness distribution). FIG. 6 is a flowchart showing a conventional separation technique for color signals. In FIG. 6, the chrominance signal (C) is a parameter represented by the chroma, or color saturation, and the color differences (I, Q). The relationship between the color difference signals (I, Q) and the luminance signal (Y) may be represented by the following equations:

$Y=0.30R+0.59G+11B$ $I=0.74(R-Y)-0.27(B-Y)$ $Q=0.48(R-Y)+0.41(B-Y)$ where R, G, B denote the brightness of each color, respectively.

Figure 7:
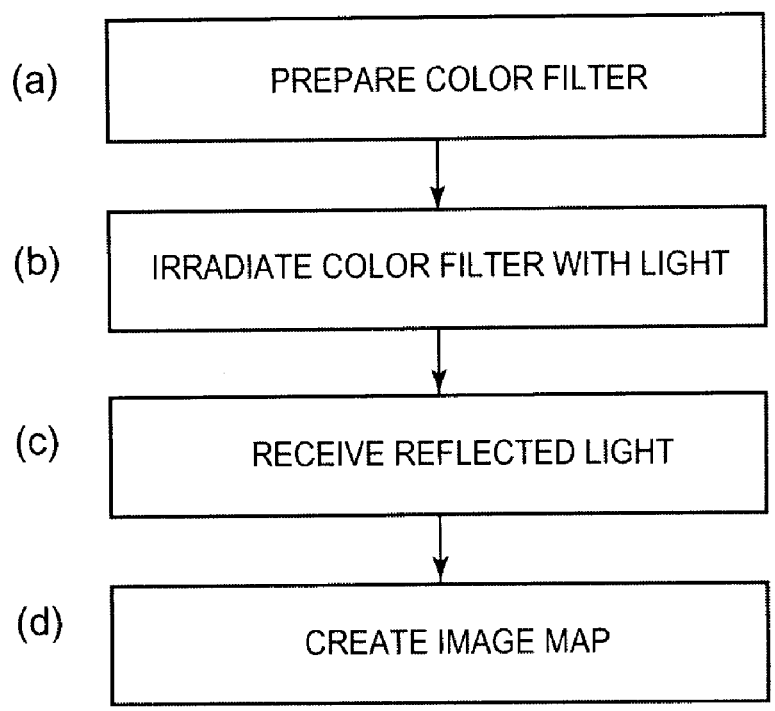
FIG. 7 is an demonstrative flowchart showing the flow of an inspection method according to one embodiment of the present invention.

FIG. 7 is a demonstrative flowchart showing the flow of an inspection method according to one embodiment of the present invention. In color-filter preparation step (a), a color filter may be placed on the plate 30 (FIG. 2). The color filter may be composed of a colored pixel array provided on a transparent substrate and an overcoat layer formed on the colored pixel array, with each colored pixel made of a resin layer in which coloring particles are dispersed. In light irradiation step (b), the light source 32 (FIG. 2) irradiates the surface of the color filter with light almost vertically from above, the light containing at least one emission line corresponding to one color of the coloring particles. In reflected-light receiving step (c), light reflected from the color filter is received by the photo-receiver 36 (FIG. 2) placed obliquely upward with respect to the surface of the color filter. Step (c) is repeated while moving the color-filter substrate according to the size of the substrate or the light irradiation range. In image-map creating step (d), an image map of the color filter (pixel array) is created from a color signal output from the photo-receiver 36 using the shades of gray of the color.

When one of multiple color signals may be extracted separately from the photo-receiver 36, a color signal corresponding to one of emission lines of the light source is selected in step (d) from output signals of the photo-receiver 36. Then, the image map is created from the color signal using the brightness (the shades of gray) of the color. In this case, the selected color signal, for example, corresponds to the color of pixels first provided on the transparent substrate. However, the color used here is not limited to that of the pixel layer first provided on the transparent substrate. For example, the second or third color of pixels may be used instead. On the other hand, when one color signal with multiple color signals combined in it can only be acquired from the photo-receiver 36, a luminance signal for a color corresponding to one of emission lines of the light source is extracted in step (d) from the output signal of the photo-receiver 36 to acquire the corresponding color signal.

Figure 8:
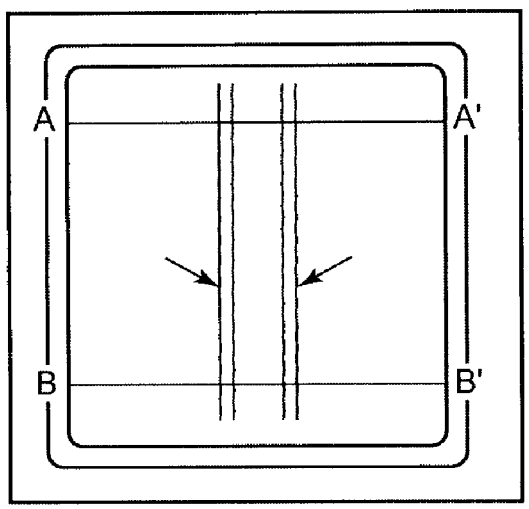
FIG. 8 shows an example of an image map obtained by the apparatus (method) of one embodiment of the present invention.

FIG. 8 is an example of the image map measured by the apparatus and/or method of one embodiment of the present invention. FIG. 8 shows an image acquired from a green color signal in one display area (screen) in the color filter. The surface of the sample of FIG. 8 is covered with the overcoat layer underneath which the colored pixel array is arranged. In FIG. 8, there are two perpendicular lines running through the center of the screen (see the arrow). The two perpendicular lines indicate an uneven surface part (uneven coating part) of the overcoat layer. This uneven coating is invisible to the unaided (naked) human eye. Only the apparatus (method) of the present invention may detect it as clear lines (an uneven pattern).

Figure 9:
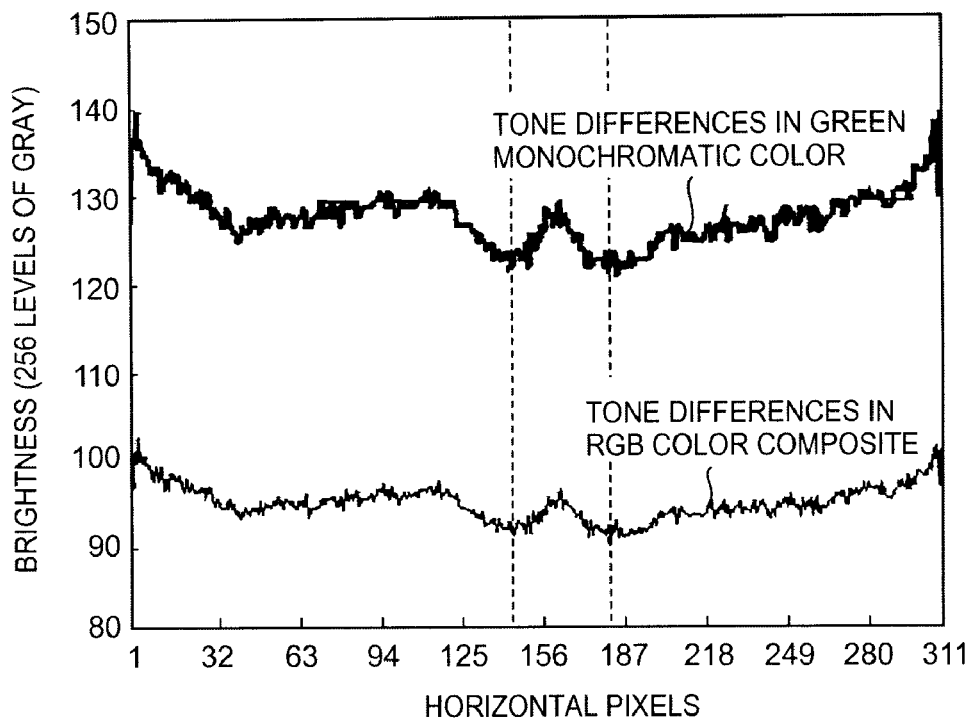
FIG. 9 is a line chart showing brightness data taken along A-A' in FIG. 8.

FIG. 9 is a line chart showing brightness distributions taken along A-A' in FIG. 8. The upper line represents tone differences (brightness distribution) in green monochromatic color, and the lower line represents tone differences (brightness distribution) in RGB color composite. The troughs in the two lines indicated by two broken lines correspond to the two perpendicular lines in FIG. 8. The peak between the two broken lines corresponds to the light (bright) area of the color between the two perpendicular lines in FIG. 8. In FIG. 9, the upper line for green monochromatic color exhibits a larger peak than that for the RGB color composite. It means that the former (use of green monochromatic color) shows higher sensitivity (higher S/N ratio).

Figure 10:
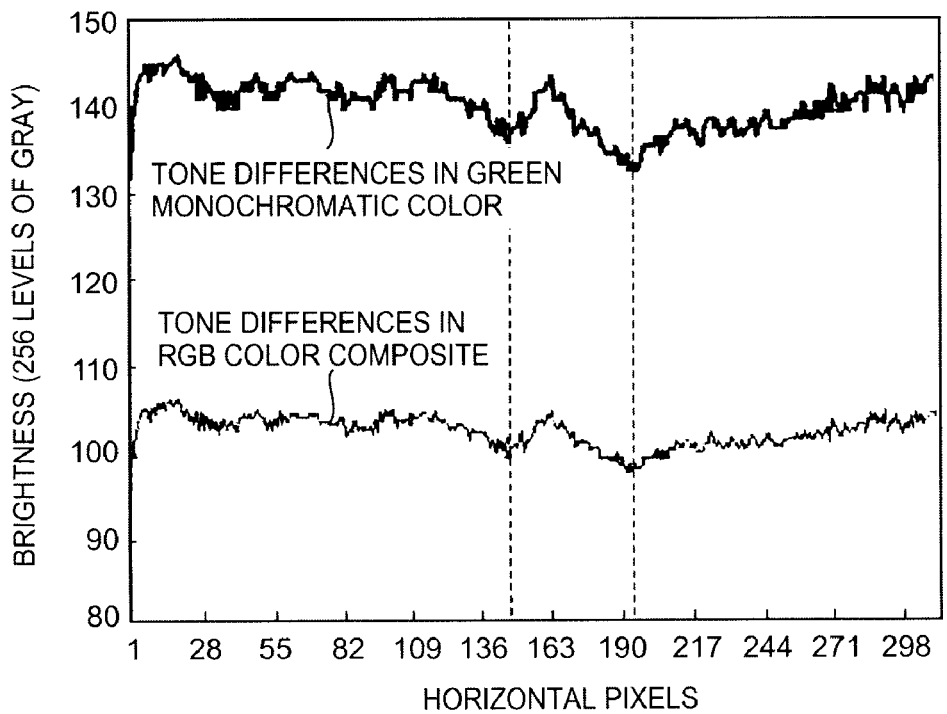
FIG. 10 is a line chart showing brightness data taken along B-B' in FIG. 8.

FIG. 10 is a line chart showing brightness distributions taken along B-B' in FIG. 8. The relationship between the upper and lower lines is the same as that in FIG. 9. These two lines also exhibit peaks similar to those in FIG. 9 between two broken lines. It is also found from FIG. 10 that the use of green monochromatic color represented by the upper line is more highly sensitive (higher in S/N ratio) than that of the RGB color composite. Thus, the presence or absence and the position of an uneven coating part of the surface of the color filter may be detected from a tone difference (brightness distribution) graph quantitatively and more clearly.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the spirit of the invention.

What is claimed is:

1. An apparatus for inspection of a color filter composed of a colored pixel array provided on a transparent substrate and an overcoat layer formed on the colored pixel array, each of colored pixels being made of a resin layer in which coloring particles are dispersed, the apparatus comprising:
a plate on which the color filter is placed;
a light source placed almost directly above the surface of the plate and having an emission-line spectrum of at least one emission line corresponding to one color of the coloring particles in the color filter;
a photo-receiver, placed obliquely upward with respect to the surface of the plate and having a spectral sensitivity corresponding to the emission-line spectrum of the light source, for receiving reflected light from the color filter on the plate during inspection; and
a detection means for creating a brightness distribution for the color using a color signal output from the photo-receiver as corresponding to its spectral sensitivity to detect flatness (unevenness) of a surface of the overcoat layer.

2. The apparatus according to claim 1, further comprising a photo-receiver moving mechanism for moving the photo-receiver to change the acceptance angle of reflected light from the color filter.

3. The apparatus according to claim 2, further comprising a plate moving mechanism for moving the plate in a horizontal direction.

4. The apparatus according to claim 1, wherein the colored pixel array is formed on the substrate by a pigment dispersion method, and the color signal output from the photo-receiver corresponds to the color of pixels first formed on the substrate.

5. The apparatus according to claim 1, wherein the light source is a monochromatic light source, and the photo-receiver has a spectral sensitivity corresponding to the monochromatic color.

6. The apparatus according to claim 1, wherein the light source has an emission-line spectrum of emission lines corresponding to all the colors of pixels, and the photo-receiver has spectral sensitivities corresponding to the respective emission lines of the light source.

7. The apparatus according to claim 1, wherein a half-bandwidth of the emission-line spectrum of the light source falls in the range of about 15-30 nm.

8. The apparatus according to claim 1, wherein the light source is a fluorescent lamp.

9. The apparatus according to claim 1, wherein the colored pixel array contains three-color pixels, namely, red pixels, green pixels, and blue pixels.

10. The apparatus according to claim 1, wherein the photo-receiver is a color line-sensor camera.

11. The apparatus according to claim 1, wherein the photo-receiver is positioned at a location where the photo-receiver does not receive specular reflection of light from the color filter.

12. The apparatus according to claim 1, wherein the detection means creates an image map of the color filter from the color signal of the photo-receiver using the shades of gray of the color.

13. An inspection apparatus for a color filter composed of a colored pixel array provided on a transparent substrate and an overcoat layer formed on the colored pixel array, each of colored pixels made of a resin layer in which coloring particles are dispersed, the apparatus comprising:
a plate on which the color filter is placed;
a light source placed almost directly above the surface of the plate and having at least one emission line corresponding to one color of the coloring particles in the color filter;
a camera, placed obliquely upward with respect to the surface of the plate and having a spectral sensitivity corresponding to an emission-line spectrum of the light source, for receiving reflected light from the color filter on the plate during inspection; and a camera moving mechanism for moving the camera to change the acceptance angle with respect to the surface of the color filter; and an image processing means for creating an image map of the color filter from the color signal output from the camera as corresponding to the one emission line of the light source using the shades of gray of the color.

14. A method of inspecting flatness (unevenness) of a surface of a color filter, the method comprising:

(a) preparing the color filter composed of a colored pixel array provided on a transparent substrate and an overcoat layer formed on the colored pixel array, each of colored pixels made of a resin layer in which coloring particles are dispersed;

(b) irradiating the surface of the color filter with light from a light source almost vertically from above, the light containing at least one emission line corresponding to one color of the coloring particles;

(c) receiving reflected light from the color filter through a photo-receiver placed obliquely upward with respect to the surface of the color filter and having a spectral sensitivity corresponding to the emission-line spectrum of the light source; and (d) creating a brightness distribution for the color from the color signal output from the photo-receiver.

15. The method according to claim 14, wherein the brightness distribution creating step (d) includes a step of selecting, from output signals of the photo-receiver, a color signal corresponding to one emission line of the light source.

16. The method according to claim 14, wherein the brightness distribution creating step (d) includes a step of acquiring, from output signals of the photo-receiver, a luminance signal corresponding to one emission line of the light source.

17. The method according to claim 15, wherein the color signal or luminance signal corresponds to the color of pixels first formed on the transparent substrate.

18. The method according to claim 14, wherein the photo-receiver is positioned at a location where the photo-receiver does not receive specular reflection of light from the color filter.

* * * * *